(12) United States Patent
Levy et al.

(10) Patent No.: US 10,751,125 B2
(45) Date of Patent: Aug. 25, 2020

(54) SIMULATION-BASED FOCUSED-ULTRASOUND TREATMENT PLANNING

(71) Applicants: Yoav Levy, Hinanit (IL); Benny Assif, Ramat Hasharon (IL); Gilad Halevy, Modi'in (IL); Yoni Hertzberg, Ben-Shemen Moshav (IL)

(72) Inventors: Yoav Levy, Hinanit (IL); Benny Assif, Ramat Hasharon (IL); Gilad Halevy, Modi'in (IL); Yoni Hertzberg, Ben-Shemen Moshav (IL)

(73) Assignee: INSIGHTEC, LTD., Tirat Carmel (IL)

( * ) Notice: Subject to any disclaimer, the term of this patent is extended or adjusted under 35 U.S.C. 154(b) by 460 days.

(21) Appl. No.: 14/763,684

(22) PCT Filed: Jan. 29, 2014

(86) PCT No.: PCT/IB2014/000382
§ 371 (c)(1),
(2) Date: Jul. 27, 2015

(87) PCT Pub. No.: WO2014/118632
PCT Pub. Date: Aug. 7, 2014

(65) Prior Publication Data
US 2015/0359603 A1     Dec. 17, 2015

Related U.S. Application Data

(60) Provisional application No. 61/757,990, filed on Jan. 29, 2013.

(51) Int. Cl.
*G06G 7/56* (2006.01)
*A61B 34/10* (2016.01)
(Continued)

(52) U.S. Cl.
CPC ............... *A61B 34/10* (2016.02); *A61N 7/02* (2013.01); *A61B 2034/101* (2016.02);
(Continued)

(58) Field of Classification Search
None
See application file for complete search history.

(56) References Cited

U.S. PATENT DOCUMENTS 8,409,099 B2 * 4/2013 Vitek .................. A61B 8/4281
600/439
8,617,073 B2 * 12/2013 Prus ........................ A61B 8/14
600/407

(Continued)

FOREIGN PATENT DOCUMENTS

| EP | 2338428 | | 6/2011 |
| EP | 2545963 | * | 1/2013 |
| WO | WO2014057388 | | 4/2014 |

OTHER PUBLICATIONS

International Search Report dated Jul. 16, 2014 for International Application No. PCT/IB2014/000382 (5 pages).

(Continued)

*Primary Examiner* — Rehana Perveen
*Assistant Examiner* — Nithya J. Moll
(74) *Attorney, Agent, or Firm* — Morgan, Lewis & Bockius LLP

(57) ABSTRACT

A focused-ultrasound or other procedure for treating a target within a tissue region can be planned iteratively by creating a treatment plan specifying a treatment location pattern and stimuli applied thereto, simulating the treatment, computationally predicting an effect of the simulated treatment, comparing the predicted effect against one or more treatment (Continued)

constraints (such as efficacy and/or safety thresholds), and, if a constraint is violated, repeating the simulation for an adjusted treatment plan.

27 Claims, 3 Drawing Sheets

(51) Int. Cl.
*A61N 7/02* (2006.01)
*A61N 7/00* (2006.01)
*A61B 90/00* (2016.01)

(52) U.S. Cl.
CPC ... *A61B 2034/104* (2016.02); *A61B 2034/105* (2016.02); *A61B 2090/374* (2016.02); *A61B 2090/3762* (2016.02); *A61N 2007/0086* (2013.01); *A61N 2007/0095* (2013.01)

(56) References Cited

U.S. PATENT DOCUMENTS

| | | | |
|---|---|---|---|
| 9,066,681 B2* | 6/2015 | Arts | A61B 18/1815 |
| 9,192,788 B2* | 11/2015 | Vahala | A61N 7/02 |
| 2009/0318804 A1 | 12/2009 | Avital et al. | |
| 2010/0179425 A1 | 7/2010 | Zadicario | |
| 2012/0191020 A1* | 7/2012 | Vitek | A61N 7/02 601/3 |
| 2012/0323599 A1* | 12/2012 | Bal | A61N 5/1031 705/2 |
| 2013/0144194 A1 | 6/2013 | Ahn et al. | |

OTHER PUBLICATIONS

Written Opinion dated Jul. 16, 2014 for International Application No. PCT/IB2014/000382 (10 pages).

* cited by examiner

SIMULATION-BASED FOCUSED-ULTRASOUND TREATMENT PLANNING

CROSS-REFERENCE TO RELATED APPLICATION

This application is a U.S. National Phase Application of PCT/IB2014/000382, filed Jan. 29, 2014, which claims priority to and the benefit of, and incorporates herein by reference in its entirety, U.S. Provisional patent Application No. 61/757,990, filed on Jan. 29, 2013.

TECHNICAL FIELD

The present invention relates, generally, to treatment planning for focused-ultrasound procedures. More specifically, various embodiments are directed to computing systems and methods for simulating and adjusting therapeutic procedures prior to execution.

BACKGROUND

High-intensity focused ultrasonic energy (i.e., having a frequency greater than about 20 kilohertz) may be used therapeutically to treat internal tissue regions within a patient. For example, ultrasonic waves may be used to induce coagulation and/or necrosis in a target tissue region, such as a tumor. In this process, the ultrasonic energy is absorbed by the tissue, causing the generation of heat. The absorbed energy heats the tissue cells in the target region to temperatures that exceed protein denaturation thresholds, usually above 60° C., resulting in coagulation, necrosis, and/or ablation of the tissue in the target region. Ultrasound can also be used for a variety of other treatment modalities, including, e.g., cavitation induced by ultrasound, neuromodulation, or controlled hyperthermia.

Focused-ultrasound methods may utilize, for example, a piezo-ceramic transducer that is placed externally to the patient, but in close proximity to the target. The transducer converts an electronic drive signal into mechanical vibrations, resulting in the emission of acoustic waves (a process hereinafter referred to as "sonication"). The transducer may be shaped so that the waves converge in a focal zone. Further, the transducer is typically defined by a plurality of individually driven transducer elements whose phases and amplitudes can each be controlled independently from one another and, thus, can be set so as to result in constructive interference of the individual acoustic waves in the focal zone. Such a "phased-array" transducer facilitates steering the focal zone to different locations by adjusting the relative phases between the transducer elements.

Focused-ultrasound treatment procedures typically require moving the focus across the target to cover the treatment area or volume, which is generally larger than the focal zone, in a series of sonications. In doing so, it is important to apply a sufficient amount of energy across the target to achieve the desired therapeutic effect while limiting accumulated energy levels in surrounding non-target tissues to avoid damage thereto. This requires detailed knowledge of the patient's anatomy in the region surrounding the target, as may be acquired, e.g., by magnetic resonance imaging (MRI). Further, it requires computational facilities to determine accurate and precise phase and amplitude settings for the individual transducer elements to focus the beam at the desired places. In many treatment scenarios, anatomical barriers, such as tissues that do not transmit or are highly sensitive to ultrasound, are located between the transducer array and the target, requiring the transducer to be either moved or driven with fewer than all elements, which further complicates the procedure. As a result, therapeutic procedures often reach a level of complexity that requires detailed advance planning to determine, based on the anticipated relative arrangement between the patient and the transducer, the phase and amplitude settings of all transducer elements as a function of time.

Conventional treatment-planning methods typically utilize a limited number of predefined sonication protocols corresponding to differently shaped focal zones, and involve "tiling" the treatment region with these shapes. Such methods, however, usually fail to account for the accumulated effect of overlapping "tiles," ultrasound absorption outside the focal zone, as well as heat transfer from the focal zone into surrounding areas. For example, to plan treatment of a three-dimensional target volume, a conventional treatment planner might slice the volume into a series of adjacent two-dimensional slices, cover each slice by a number of predefined sonications, and compute the energy for each sonication based on the desired dose in the respective slice. During treatment, however, each slice absorbs energy not only from sonications focused at the slice, but also from sonications directed at neighboring slices. Consequently, the total amount of energy deposited in the slice may exceed that previously calculated. While such excessive heating may not have a detrimental effect for treatment of the target itself (e.g., because the desired treatment effect is target ablation), it may cause surrounding non-target tissues to be exposed to an unnecessarily high amount of ultrasound energy. Accordingly, it is desirable to add up all contributions to the heating of any region in order to set the energy delivered per sonication to a level no larger than necessary to effect treatment.

To some extent, a previously planned treatment procedure can be corrected during treatment based on real-time information about the treatment effect. MRI, for example, is not only useful to visualize the focus and/or target in order to guide the ultrasound beam, but can also be employed in various thermometry techniques to monitor the temperature distribution in a region including the target to ensure that it remains at a desired level or within a desired range (e.g., above an efficacy threshold in the target region and below a safety threshold in non-target tissues). If the temperature in the target is too low, additional sonications may be applied to reach the desired efficacy threshold. Conversely, if the temperature in a non-target region, or a target region to be treated nondestructively (e.g., for palliative purposes, or for controlled hyperthermia), is too high, a waiting period may be introduced to allow the tissue to cool off. In some circumstances, however, irreversible damage may already have been done following absorption of too much energy by a non-target tissue. Further, any adjustments to the sonication procedure during treatment based on a measured effect result in prolongation of the overall treatment time, which may not only strain the patient's patience, but also introduce errors, e.g., due to inadvertent but inevitable patient movements.

Accordingly, there is a need for systems and methods that facilitate more accurate planning of focused-ultrasound procedures for complex treatment scenarios including multiple clinical and anatomical constraints, taking into account ultrasound absorption outside the desired target region and heat transfer across the tissue.

SUMMARY

Embodiments of the present invention are directed to treatment-planning methods that involve simulating the planned procedure computationally and, typically, adjusting the procedure iteratively based on the simulated effect, as well as to hardware and/or software for implementing such methods (hereinafter collectively referred to as the "treatment planner" or "planner"). In various embodiments, the treatment procedure involves multiple treatment methods; for example, an ultrasound procedure may include sonications applied to achieve the therapeutic effect in the target tissue and, complementary thereto, active cooling of tissue surfaces to protect non-target tissues. Further, while the ensuing description focuses on ultrasound procedures, various concepts, embodiments, and features disclosed herein are also applicable to other therapeutic methods, such as, e.g., radio-frequency (RF) ablation, radiation therapy, or hyperthermia inducement, and such applications are, accordingly, within the scope of the invention.

The simulation generally includes modeling a tissue region of interest and a treatment configuration, computationally applying treatment stimuli, and computationally predicting the effect of the stimuli, typically as a function of time. The tissue region includes the target and, typically, non-target tissues—e.g., tissues surrounding the target and/or tissues located, in the case of ultrasound stimuli, between the transducer and the target. In general, the treatment configuration specifies the geometry as well as the position and orientation of the transducer (or other treatment device) relative to the target. The stimuli may include, e.g., a series of sonications at desired focus locations or along a desired focus path and, optionally, thermal stimuli conductively applied to tissue interfaces (e.g., via physical contact thereat with a cooling pad or fluid conduct). Stimuli may also be chemical in nature, e.g., in the case of drug activation or release. Predicting the effect of the stimuli generally includes modeling the propagation of a locally induced effect through the tissue region (or a portion thereof).

The stimuli and treatment effect may be characterized by various physical, biophysical, or biochemical parameters, depending on the particular treatment modality and the desired precision and resolution of the simulation. For example, a series of sonication pulses applied at discrete foci may be described in terms of the total energies delivered to the focal locations, or, for greater spatio-temporal resolution, in terms of the intensity distributions within the focal zones over the pulse duration. Similarly, a continuous sonication applied along a focus path across the target may be described in terms of the power and/or intensity of the sonication as a function of time and/or position along the path. Active cooling may be captured by specifying the temperature at boundaries in contact with cooling reservoirs. In embodiments where the treatment is primarily based on mechanical (as opposed to thermal) energy, the stimuli and/or treatment effect may be described in terms of pressures, forces, a mechanical index, or mechanical stresses. For treatment modalities that affect chemical or biological tissue conditions, the treatment effect may be captured with suitable chemical or biological parameters. For example, drug delivery may be described in terms of local concentrations of the drug. In general, suitable parameters used to characterize and quantify the stimuli and/or treatment effect may be selected based on the treatment modality. In addition to tissue ablation or coagulation by heat or mechanical impact, ultrasound-based treatment modalities include, without limitation, cavitation (which can have several effects on the surrounding tissue, including, e.g., opening physiological barriers such as the blood brain barrier), neuromodulation (e.g., neurological stimulation or neurological inhibition), targeted drug delivery (e.g., via activation of drugs or disruption of barriers, such as the blood brain barrier, to increase drug uptake), or the triggering of other chemical or physiological activities (e.g., by causing controlled hyperthermia).

In various embodiments, the computed effect of a simulated treatment procedure is compared against one or more treatment constraints, such as a minimum temperature, power, or energy required in the target tissue to achieve a desired treatment effect (an example of an "efficacy constraint") or a maximum temperature allowed in non-target regions to stay within a safe regime (an example of a "safety constraint"). Efficacy constraints may be imposed, e.g., in terms of a minimal temperature, minimal thermal dose, minimal acoustic power, minimal acoustic energy, required acoustic wave pattern, maximal distance from sonication foci, or minimal mechanical index. Safety constraints may specify, e.g., a maximal temperature, maximal thermal dose, maximal acoustic power, maximal acoustic energy, allowed or prohibited acoustic wave pattern, minimal distance from sonication foci, maximal mechanical index; minimal distance from an area in which a safety constraint is violated, etc. If one or more of the constraints are violated during the simulation, the simulated treatment procedure is adjusted. Such adjustment generally takes one of two forms: the treatment plan can either be "rolled back" so as to modify previously set treatment parameters, or the existing portions of the procedure are retained but the plan is extended to include further sonications (or other treatment steps). For example, if the simulation generates temperatures in the target region below an efficacy threshold, this can be remedied by increasing the energy or intensity of the planned sonications in the target, and/or by adding more sonications at the target. Conversely, if the computed temperature in a non-target region approaches or exceeds a safety threshold, suitable modifications to the treatment plan may include a reduction of the energy or intensity of sonications applied to the target, a decrease in the temperature of any active cooling medium, and/or—if the temperature has not yet reached levels where tissue damage occurs, but is dangerously close thereto—the incorporation of a cooling-off period in the treatment plan. The treatment plan may be simulated and adjusted iteratively until the simulated treatment effect no longer violates any of the treatment constraints. (If it turns out that the initially set treatment constraints are unattainable, the constraints may be relaxed during planning to nonetheless allow for completion of the treatment plan. In some cases, the initial constraints are aspirational and serve to iteratively optimize the plan; when iterative treatment-plan adjustments no longer result in improvements, any constraints that are still violated may be dropped (assuming they are within acceptable absolute levels) and the treatment plan is deemed finalized. Of course, in some instances, strict adherence to the treatment constraints is important for patient safety, and if modifications to the treatment plan cannot cure constraint violations, treatment planning is aborted as unsuccessful.)

Following completion of the treatment plan, the treatment may be carried out in accordance with the plan. In some embodiments, the treatment effect is monitored during treatment (e.g., by means of MRI-based or other types of thermometry) to ensure that it does, indeed, remain within the treatment constraints. If discrepancies between the measured treatment effect and the previously computed treatment effect are discovered, the treatment plan may be modified. Discrepancies may arise, for example, from inaccuracies in certain parameters of the physical model underlying the simulation, such as, e.g., absorption coefficients.

Accordingly, the measurements taken during actual treatment may be used as feedback to adjust the parameters. A new treatment plan may then be generated using the adjusted parameters. Alternatively, in various circumstances, a straightforward adjustment of the existing treatment plan may be carried out, e.g., by propagating the adjustment of the parameter(s) through the model.

Accordingly, in one aspect, the invention relates to a method of planning focused-ultrasound treatment of a target tissue within a tissue region. The method includes creating a treatment plan at least in part by specifying (i) a focus pattern corresponding to at least a subregion of the target tissue and (ii) temporally variable ultrasound stimuli to be applied sequentially along the focus pattern. The focus pattern may be, e.g., a distribution of discrete focal points, a continuous focus path or plurality of focus-path segments (i.e., straight or curved lines along which the focus is swept during treatment), or any combination thereof. (The ultrasound stimuli are temporally variable if, for a distribution of focal points, the stimuli differ (e.g., in the applied energy) between at least two points of the pattern as the pattern is traversed, and, for a continuous focal path, the ultrasound stimuli vary (e.g., in the applied power) along the path as the path is traversed.) The method further includes simulating treatment in accordance with the plan at least in part by computationally traversing the focus pattern and computationally applying the temporally variable ultrasound stimuli thereto; computationally predicting an effect of the simulated treatment based, at least in part, on a physical model computationally modeling propagation of the effect; comparing the predicted effect against at least one treatment constraint (e.g., a treatment constraint and/or a safety constraint); and, if the at least one treatment constraint is violated, altering the treatment plan (by altering the focus pattern and/or at least one of the ultrasound stimuli applied thereto), and repeating steps (b) through (e) for the altered treatment plan.

Creating the treatment plan may further include defining parameters of a complementary treatment procedure, such as, e.g., active heating or cooling. The physical model may include one or more parameters of the tissue region (e.g., absorption coefficients) and/or one or more equations modeling ultrasound absorption and heat transport in the tissue region. Predicting the effect of the simulated treatment may include modeling propagation of the effect to a non-target tissue within the tissue region. In some embodiments, the above treatment-planning steps are successively carried out for a plurality of subregions of the target tissue; in this case, the prediction may also involve modeling propagation of the effect into another subregion of the target tissue. The treatment effect may be or include, e.g., heating of the tissue region due to ultrasound absorption and heat transport, or generally any effect that changes a (thermal, mechanical, chemical, or other) property or condition of the tissue. The treatment constraint(s) may include a tissue-damage threshold, a treatment-efficacy threshold, and/or geometric parameters of heat-sensitive tissues. Following comparison of the predicted effect against the treatment constraint(s), treatment planning and simulation may be repeated for the entire subregion. Alternatively, in some embodiments, they are repeated for only a portion of the focus pattern, and adjustments to the temporally variable ultrasound stimuli are confined to stimuli to be applied along that portion.

In some embodiments, the method further comprises using a treatment device to conduct a first portion of the treatment in accordance with a first portion of the treatment plan; experimentally monitoring the effect of the conducted treatment; comparing the experimentally monitored treatment effect with the predicted treatment effect; and, upon detection of a discrepancy between the experimentally monitored treatment effect and the predicted treatment effect, adjusting the physical model (e.g., by adjusting one or more parameters thereof), revising the treatment plan based on the adjusted model, and then conducting a second portion of the treatment in accordance with the revised treatment plan. Revising the treatment plan may involve repeating the creation of the treatment plan, simulation of the treatment, prediction of the treatment effect, comparison of the predicted effect against treatment constraints, and adjustment of the treatment plan if a constraint is violated with the adjusted model; alternatively, in some embodiments, the treatment plan can be revised without repeating these steps to re-plan treatment.

In another aspect, embodiments provide a system for planning focused-ultrasound treatment of a target tissue within a tissue region. The system includes a processor, and memory storing (i) data descriptive of a model of the tissue region and at least one treatment constraint, as well as (ii) a treatment plan specifying a focus pattern corresponding to at least a subregion of the target tissue and temporally variable ultrasound stimuli to be applied sequentially along the focus pattern. The memory further stores instructions which, when executed by the processor, cause the processor to simulate treatment in accordance with the stored treatment plan at least in part by computationally traversing the focus pattern and computationally applying the temporally variable ultrasound stimuli thereto; computationally predict an effect of the simulated treatment based on the data descriptive of the model of the tissue region and a physical model modeling propagation of the effect; compare the predicted effect against the at least one stored treatment constraint; and, if the at least one treatment constraint is violated, (i) alter the treatment plan and (ii) repeat steps (a) through (d) for the altered treatment plan.

Yet another aspect pertains, more generally, to a method of planning treatment of a target tissue within a tissue region. The method includes electronically storing a treatment plan specifying (i) a treatment location pattern corresponding to at least a subregion of the target tissue and (ii) temporally variable treatment stimuli to be applied sequentially along the pattern; using a computer simulating treatment in accordance with the plan at least in part by computationally traversing the treatment location pattern and computationally applying the temporally variable treatment stimuli thereto; computationally predicting an effect of the simulated treatment based on a physical model computationally modeling propagation of the effect; comparing the predicted effect against at least one treatment constraint; and, if the at least one treatment constraint is violated, altering the treatment plan and repeating, for the altered plan, the steps of simulating treatment, predicting an effect thereof, comparing the predicted effect against a treatment constraint, and, if necessary, altering the treatment plan again.

BRIEF DESCRIPTION OF THE DRAWINGS

The foregoing will be more readily understood from the following detailed description of the invention, in particular, when taken in conjunction with the drawings, in which.

DETAILED DESCRIPTION

Figure 1:
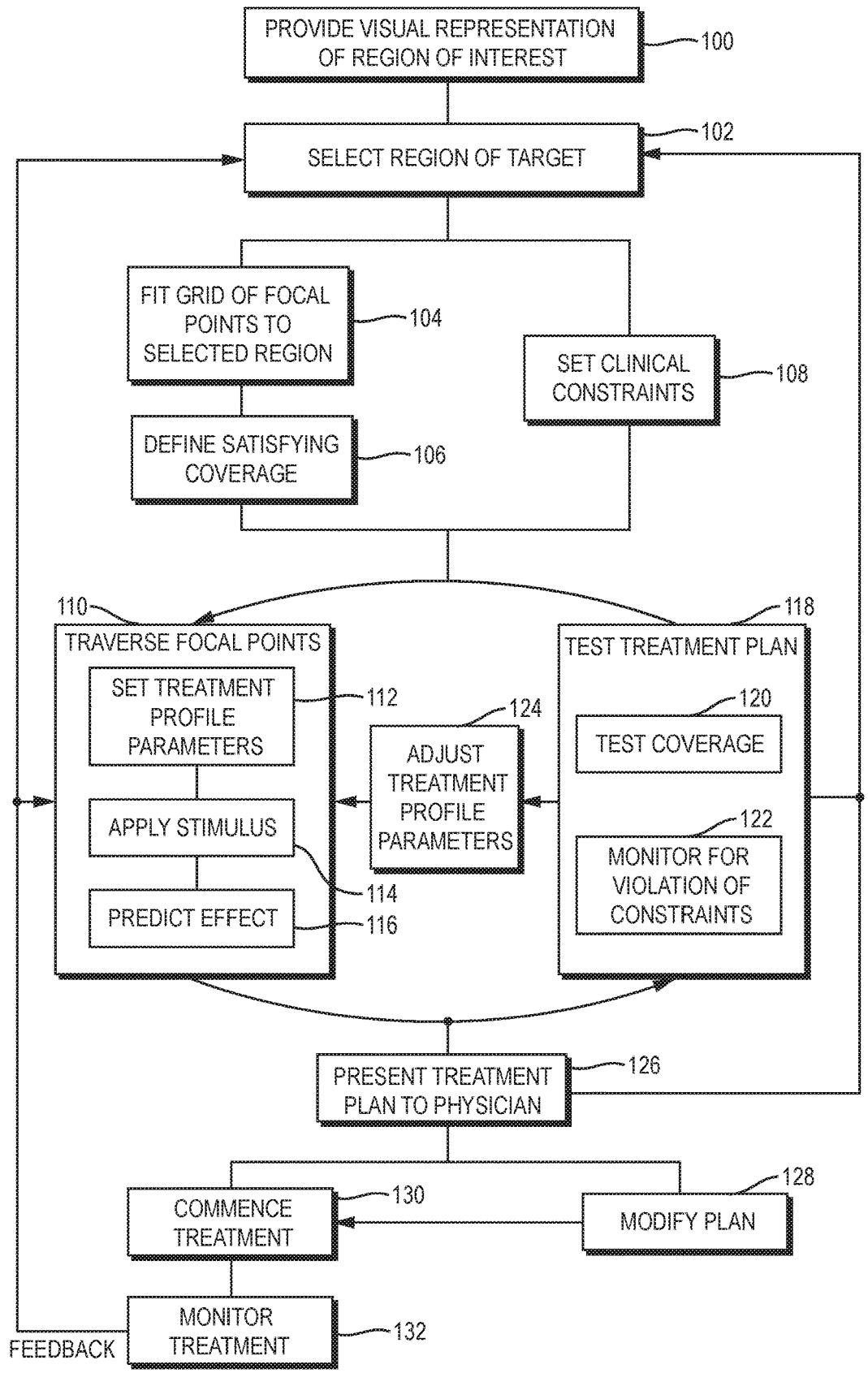
FIG. 1 is a flow chart illustrating treatment planning methods in accordance with various embodiments.

Various embodiments hereof provide methods for planning focused-ultrasound treatment of one or more target tissues within a tissue region that may also include non-target tissues. Treatment planning often has the dual goals of achieving the desired treatment effect in the target tissue(s) while at the same time avoiding damage to non-target tissues. FIG. 1 illustrates, in the form of a flow chart, an exemplary treatment-planning method in accordance with various embodiments. As shown, treatment planning may begin, in step 100, with providing a visual representation of the patient's anatomy within a region of interest to the treating physician. The visual representation may, for example, include or consist of a series of image slices acquired with MRI, computed tomography (CT), ultrasound, or any other medical imaging modality, or a three-dimensional graphical model created based on such images. In step 102, the physician identifies a target, or portion of a target, within the region of interest, e.g., by overlaying an outline around the organ to be treated on the image (or a series of images). Such an outline may be directly drawn by the physician using a suitable drawing interface (e.g., a touch screen that allows the physician to trace the organ boundaries in the image with her finger or a suitable stylist), or be computer-generated, based on a physician-made selection (e.g., clicking on the target organ), using image-segmentation or other suitable image-processing techniques.

In various embodiments, treatment planning is performed sequentially for multiple individual regions that collectively constitute the overall target, and the physician may, in step 102, select the region for which treatment is to be planned next. In some treatment scenarios, the target consists of multiple discontiguous regions; for example, a cancer patient may be afflicted with multiple tumors or metastases that are to be treated individually. Even if the target is a single, contiguous tissue region, it may be divided, for planning and/or treatment purposes, into multiple (disjunctive or overlapping) regions. For example, in many situations, it is advantageous to treat a three-dimensional target volume in slices, which may provide better control over beam properties despite tissue heterogeneities in the target resulting from treatment (e.g., to avoid beam aberrations, the slice most distant from the transducer may be treated first), allow covering the target volume with minimal mechanical maneuvering (e.g., minimal adjustments to the position and orientation of the transducer during treatment), and facilitate monitoring treatment of each slice without requiring any change of the imaging plane. In various advantageous embodiments, the target is divided in a manner that allows treatment planning for the different regions to be performed sequentially, possibly taking the effect of treatment of one region into account when planning treatment for subsequent regions, but without incurring the risk of a need to revisit a treatment procedure for a region for which treatment planning was previously deemed complete.

Once the physician has selected a region (e.g., the target or a subregion thereof) for treatment planning, a focus pattern that covers the region may be fitted to the region (step 104). For example, the treatment planner may fit a grid of focal points to the region such that focal zones located at the grid points collectively cover the region (with or without overlap between the zones). (For purposes hereof, a focal zone may defined as a contiguous region around a focus point that is bounded by a fall-off in the intensity to half, or some other specified fraction, of the maximum intensity.) In certain embodiments, the region may be adequately covered with a two-dimensional distribution of focal points; in general, however, the grid of focal points is three-dimensional. During treatment, ultrasound will be sequentially applied to all the grid points in an order determined during the planning stage. In alternative embodiments, the focus pattern includes, instead of a set of discrete focus locations, one or more continuous focus paths within the target; in this case, treatment involves moving the ultrasound focus along the path(s) (again, in the case of multiple path segments, in an order specified during planning) and thereby sweeping the focal zone across the target. The focal paths may be configured, in two or three dimensions, such that the focal zone has covered the entire (or substantially entire) region once all paths have been traversed. The locations of the focal points and/or paths may be computed taking into account the patient's overall anatomy, the shapes and locations of the target and any relevant non-target organs or tissues, and/or the transducer location. Further, while the focus pattern is generally determined autonomously by the planner using suitable algorithms, it may, in some embodiments, be adjusted based on physician input. For example, the physician may, based on his experience, manually tweak the density of grid points or paths in certain subregions.

In some scenarios using discrete focus locations, the focal spot created by an individual focused beam is too small to be meaningful for clinical and/or simulation purposes. In these cases, a group of (e.g., on the order of ten) foci arranged in a fixed pattern in the vicinity of a grid point and collectively forming a contiguous zone may be treated collectively as one focus at the grid point with a corresponding focal zone; the individual foci are then referred to as "sub-foci." In other words, the focal zone at a grid point may be created by sequentially focusing the beam, or simultaneously focusing multiple beams (which may, e.g., be created with multiple segments of an ultrasound transducer array), at the plurality of "sub-foci." Hereinafter, ultrasound application at a group of sub-foci belonging to the same focal zone is considered a single sonication, and no distinction is made between a sonication created by a single focus and a sonication created by a group of sub-foci.

After covering the treatment region with a grid of focal points or other focus pattern, the treatment planner imposes (e.g., based on user input) various treatment constraints. In step 106, a treatment efficacy threshold, or "satisfying coverage," for the region is defined—e.g., in terms of a temperature or thermal dose required to achieve the desired therapeutic effect (such as, e.g., ablation of the target tissue). The treatment efficacy threshold may vary depending on position. For example, for focal points far away from sensitive organs, the treatment planner will generally apply more aggressive criteria to assure treatment efficacy.

In step 108, which may precede or follow the determination of the focus pattern and the satisfying coverage, clinical constraints may be set. Clinical constraints include both inherent anatomical constraints (such as, e.g., ultrasound barriers such as reflective tissues) that that affect beam paths, treatment windows, and transducer placement, and treatment constraints that are deliberately imposed to ensure that treatment of the target area is conducted safely, i.e., without causing significant damage to other areas (or, in certain non-destructive treatment modalities, without damaging the target itself). Such safety-based constraints may, for example, specify maximum pressures, energy densities, heat doses, or temperatures and/or allowable deviations from targeted temperatures, energy doses, etc., and may require avoidance of pressure profiles that might cause, e.g., undesired cavitation or neuromodulation. (While primarily imposed for the protection of non-target tissues, the target tissue itself may also be subject to safety-based constraints, e.g., to avoid boiling of the target.) Since different biological organs generally differ in their sensitivity to heat, mechanical stress, acoustic energy, and other effects of ultrasound-tissue interaction, as well as in the severity of health risks associated with their damage, safety thresholds and constraints may be defined separately for each tissue type. Further, as an additional measure of caution, some constraints may be extended from a sensitive organ or tissue itself into the surrounding area to provide a spatial safety margin; for example, a thermal dose exceeding a specified threshold amount may not be allowed within a specific distance of a sensitive tissue. Clinical constraints may be defined by the treatment planner based on pre-programmed criteria and data, manually set by the physician, or determined by the treatment planner based on physician input.

In controlled-hyperthermia applications, the temperature in the treatment target needs to be controlled between lower and upper boundaries, which can be set in an analogous manner as described above; here, the lower boundary corresponds to the satisfying coverage (i.e., the minimum energy that needs to be applied to achieve a treatment effect) and the upper boundary corresponds to a safety constraint. However, in contrast to tissue ablation and necrosis applications, where the lower boundary (below which the temperature may not fall) applies to the target and the upper boundary (which may not be exceeded) usually applies to the surrounding healthy tissue, upper and lower boundaries in hyperthermia treatment generally apply both to the same region, i.e., the target. Consequently, the lower boundary in hypothermia is below the upper boundary, whereas for tissue ablation, the upper boundary applied to non-target tissues may be lower than the lower boundary applied to target tissue.

Other types of treatment constraints may be imposed depending, in general, on the particular treatment modality and application. In ultrasound-induced cavitation, for instance, constraints may be imposed on the number or density of bubbles generated in the tissue, the properties of the bubbles, and/or the mechanical index affected thereby. In neuromodulation scenarios, constraints may preclude particular focal patterns or family of patterns for certain regions of the brain, if ultrasound simulation along such patterns would induce an undesirable neurological response.

Based on the focus pattern, the satisfying coverage levels, and the clinical constraints, the treatment planner determines treatment profile parameters for the sonications at each focal point, i.e., at each discrete focus or at each point (with a given spatial resolution) along a continuous focus path. The treatment profile may include parameters characterizing sonication performance, such as sonication power, acoustic field shape, or the length of the sonication, as well as parameters characterizing the transducer settings for each sonication, such as transducer position and/or orientation and phase and/or amplitude settings for individual transducer elements. Generally, the treatment profile parameters may be functions of both the focal position and the treatment stage or time during treatment (as the same spatial focus position may be reached at different times during treatment), and depend on the target location and clinical constraints. The planner typically determines the treatment profile parameters iteratively (beginning with initialized parameter settings), using simulations of the treatment and its effect to adjust the parameters in successive iterations. For example, in embodiments utilizing a grid of focal points, the planner may, as shown, traverse the grid of focal points according to some predefined logic (step 110), and, for each point traversed, set treatment profile parameters (step 112). An ultrasound stimulus may then be computationally applied in accordance with the set parameters (step 114), and the effect of the stimulus (step 116) may be computationally predicted. Thus, an overall treatment plan may be gradually built up from sonications at the individual focal points. More generally, the planner may computationally traverse the focus pattern and apply ultrasound stimuli along the way in accordance with current parameter settings. Treatment planning may also include specifying parameters not related to a specific focal point, such as, e.g., waiting time periods during which no sonication takes place.

In some embodiments, the ultrasound treatment procedure is complemented by another treatment modality, such as active cooling (or heating) using, e.g., flow of a cooling fluid through tubing in contact with the skin or another accessible tissue surface or interface. In this case, treatment planning may further involve setting parameters of the complementary treatment modality, e.g., the temperature and/or flow rate of the cooling fluid. Further, computation of the treatment effect takes the complementary modality into account such that the joint effect of, e.g., ultrasound application and active cooling is simulated. Other treatment modalities that may complement ultrasound treatment include, e.g., controlled release of a drug or contrast agent, controlled ventilation, controlled anesthesia, or controlled visual stimuli presented, e.g., on a screen to provide instructions, cognitive tasks, or entertainment to the patient. All of these procedures may have an effect on the treatment and may, therefore, be accounted for in the model (which may, in this case, go beyond a physical model and include, e.g., psychological mechanisms). For example, a video shown to the patient may reduce (or, alternatively, ask the patient to impose) motion. Videos and other visual stimuli can also cause activity in neural networks (and blood flow), which is generally relevant to models related to neuromodulation. Controlled drug release is important for modelling targeted drug delivery and blood brain barrier disruption. Ultrasonic contrast agents generally interact with the acoustic beam and may change the effect of the beam. A ventilator may change the anatomical configuration in areas that are affected by the respiratory cycle. Anesthesia may change clinical constraints as it can potentially make the patient more tolerant, e.g., to decreased or increased tissue temperatures.

The simulation of the sonications (or other treatment stimuli) and their effect on the tissue (steps 114 and 116) is, in various embodiments, based on a parameterized physical model. The physical model may include volumetric distributions of certain material properties or other physical quantities, such as, e.g., the speed of sound, or tissue coefficients characterizing acoustic absorption, transmission, and impedance; the values of these distributions may vary spatially depending on tissue type, temperature, the patient's oxygen saturation level, or other environmental conditions. Further, the physical model may include one or more equations that describe the absorption of ultrasound in the tissue; the conversion of ultrasound energy or pressure into heat, tissue displacement, or other effects; and/or the propagation of the induced effect through the tissue. Typically, these equations take the form of differential equations; examples include diffusion and heat equations.

In some embodiments, a bioheat equation is used to simulate heat transport from a focal zone into the surrounding tissue via convection through the blood stream and/or conduction. For example, the Pennes model of heat transfer in perfused tissue, or a modification thereof, may be employed. The Pennes model is based on the assumption that the rate of heat transfer between blood and tissue, $h_b$, is proportional to the product of the blood perfusion rate $W_b$ (measured in kg/(s·m$^3$)) and the difference between the arterial blood temperature $T_a$ and the local tissue temperature $T(x, y, z)$: $h_b = W_b C_b (T_a - T)$, where $C_b$ is the specific heat of blood (measured in J/(K·kg)). Adding a heat-transfer contribution due to thermal conduction in the tissue, and taking into account metabolic heat generation at a rate $Q_m$ (measured in J/(s·m$^3$)), the Pennes equation expresses the thermal energy balance for perfused tissue in the following form:

$$\rho C \frac{\partial T}{\partial t} = k \left( \frac{\partial^2 T}{\partial x^2} + \frac{\partial^2 T}{\partial y^2} + \frac{\partial^2 T}{\partial z^2} \right) + W_b C_b (T_a - T) + Q_m,$$

where $\rho$, C, and k are the density, heat capacity, and thermal conductivity (measured in J/(s m K)) of the tissue, respectively. Within a certain type of tissue, the tissue parameters can, for many practical applications, be assumed to be uniform throughout the tissue; however, certain parameters, such as the metabolic heat generation rate, may vary as a function of time. In regions spanning multiple types of tissue, the tissue parameters usually vary also spatially. To include the effect of ultrasound applied to a focal zone, which amounts to an external heat source, the Pennes equation may be modified by inclusion of an additional term $Q_{ext}$, which is, generally, a function of spatial coordinates and time:

$$\rho C \frac{\partial T}{\partial t} = k \left( \frac{\partial^2 T}{\partial x^2} + \frac{\partial^2 T}{\partial y^2} + \frac{\partial^2 T}{\partial z^2} \right) + W_b C_b (T_a - T) + Q_m + Q_{ext}.$$

In principle, the term $Q_{ext}$ may also include the effect of heat sinks (i.e., cooling), as long as the thermal power extracted per unit volume of tissue can be quantified; practically, however, cooling (e.g., applied to the skin) is often more appropriately taken into account via suitable boundary conditions (e.g., a fixed temperature at the skin). Additional modifications to the Pennes equation may be made. For example, for certain applications, metabolic heat generation may be negligible, allowing the equation to be simplified by dropping the term $Q_m$.

In some embodiments, an experimental model, derived from measurements and/or general observations, is used either in lieu of or supplementing a physical model. Measurements may also be used to specify variable parameters in the model. For example, tissue densities or other physiological properties may be discerned from MR images, and temperatures may be determined in discrete places using temperature sensors or across areas and volumes using MR thermometry. In various embodiments, patient- and treatment-specific information, such as patient-specific anatomical models or the locations of ultrasound transducers and cooling equipment in specific therapeutic setups, is used, e.g., to establish boundary conditions for the solution of the model equations.

Returning to FIG. 1, once an initial treatment plan, or portion thereof, has been created (in step 110), it may be tested computationally (step 118) for violation of any constraints, i.e., often for both treatment efficacy and safety. To determine whether satisfying coverage has been achieved, it is generally not necessary to consider the effect of the sonication for each voxel within the simulated volume; rather, it may suffice to test coverage at one or more representative points. Similarly, to evaluate whether the treatment plan is within the clinical (e.g., safety) constraints, it may be sufficient to consider temperatures and other relevant parameters at a set of representative locations, e.g., within an outer layer of a sensitive tissue. The number and locations of the control points may depend on the positions of the target and the transducer, the patient's anatomy, the focal-point grid or other focus pattern, and the stage during planning. For example, after a first iteration of treatment planning, a small number of control points may suffice to provide feedback for the next iteration, whereas further refinement after multiple iterations may require more extensive testing—in particular, to ensure that no safety constraint has been violated. On the other hand, once testing confirms that satisfying coverage within a certain area has been achieved, this area may not need to be tested for coverage again after the next iteration.

The computational "measurements" of the temperature, accumulated thermal dose, or other parameter at various control points provide insight into the efficacy and safety of the present treatment plan. Accordingly, they may be used to adjust the treatment profile parameters (step 124) and thereby refine the plan. For example, if the energy deposited at a certain focal point has not reached the specified efficacy threshold, additional energy may be applied at that focal point, either by correcting the initially set thermal dose upwards, or by adding an additional sonication at the same location. In the former case, execution of the treatment plan will involve only one sonication at the focal point at issue, whereas in the latter case, the treatment procedure itself will involve returning to the focal point at issue after traversing other focal points and/or after some time has passed. If the testing reveals violation of a safety constraint, e.g., overheating of a sensitive tissue, the planner typically "rolls back" the part of the planned treatment that caused the problem and repeats the treatment planning process for a number of focal points (or, more generally, a portion of the focal path) while reducing the applied thermal doses. This possibility of rolling back treatment is a major advantage of detailed treatment planning in accordance herewith prior to actual treatment. When a constraint violation due to overexposure is detected during an actual treatment procedure, it is, or course, too late to avoid the problem. Detection of the constraint violation serves, in this case, mere damage control—for example, the treatment procedure may be aborted to avoid exacerbating the problem through continued heating. The simulation of treatment ahead of time, by contrast, allows for the retroactive correction of a problem detected in one run and, thus, the proactive prevention of the same problem in a subsequent run of the simulation. Roll-back may be complete or partial: in some embodiments, once a constraint is violated, the previously determined treatment profile parameters are discarded and the traversal of focal points (step 110) starts over; in other embodiments, only a portion of the treatment plan is rolled back. For example, in one embodiment, the plan is kept by and large as is, except that the energy at one or a few focal points responsible for the constraint violation is reduced, and if subsequent testing reveals that the reduction was insufficient, further reductions are applied.

Figure 2:
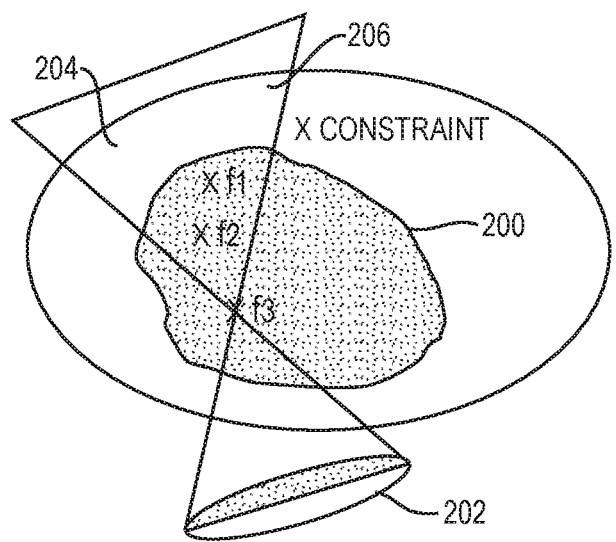
FIG. 2 is a schematic diagram illustrating an exemplary treatment scenario in accordance with one embodiment.

Refer to FIG. 2, which illustrates an exemplary scenario that may require roll-back in treatment planning. The shaded area indicates the region 200 to be treated, which includes the three marked focal points f1, f2, and f3. When the transducer 202 focuses ultrasound at any of the three focal points, its far field 204 overlaps with a non-target region 206 that is subject to a constraint X (e.g., a maximum allowable thermal dosage). Assume that the planner previously put 1000 Joules at each focal point f1 and focal point f2. Assume further that, when the planner then attempts to put some energy at focal point f3 to cover the lower part of the region 200, the constraint X is violated due to the small contribution of the beam focused at f3 to the overall thermal dose inadvertently delivered to the non-target region 206. Rather than terminating the planning at this time and avoiding any sonication at f3, the planner may revise the previous sonications. Determining that the sonication at f1 has the greatest effect on the non-target region 206, the planner reduces the amount of energy focused at f1, re-simulates heat propagation to obtain updated values for the thermal dose accumulated at various control points in the target and non-target regions 200, 206, and continues with the planning, e.g., now adding a sonication at f3 to cover the lower part of the region 200. Going back and forth in treatment time to revise the treatment plan, it is often possible to improve coverage while satisfying safety constraints. Note that reducing the energy at f1, compared to the originally planned amount, does not necessarily compromise coverage in that portion of the target region 200. First, the energy in the originally planned sonication may have been set too high to assure treatment efficacy. Second, the residual energy at f1 due to sonications at f2 and f3 may compensate for the decreased amount focused directly at f1. If it is, however, not possible to provide the desired coverage throughout the target region 200 without violating the constraint, f1 is likely the best point to compromise on as it effects the area subject to the constraint the most. In fact, the planner may routinely leave focal points before achieving satisfying coverage in order to provide a better overall energy distribution; if certain focal points need additional energy after sonication over a larger area has been planned, the planner can return to these focal points.

Referring again to FIG. 1, treatment planning is, generally, an iterative process that may utilize testing of the simulated treatment plan at various stages. In particular, the planner need not have traversed the entire grid of focal points before it computationally evaluates coverage and safety of the treatment plan. Following each test (step 118), the planner may continue with the next sonication (often basing the treatment profile parameters of subsequent sonications on the results of the test), go back to adjust a previous sonication (or repeat sonication at a previously covered focal point), or even switch the planning to an entirely new region (e.g., return to step 102, which allows the physician to select a region within the target for planning) Finally, testing may reveal that satisfactory coverage has been achieved for the region to be treated without violating any clinical constraints, and planning for the region is complete. Alternatively, the planner may determine that the iterative process is not converging (i.e., adjustments to the treatment plan cannot simultaneously satisfy all treatment constraints). In this case, planning for the region may nonetheless be deemed complete if, for instance, the violations are minor (which amounts to relaxing the constraints), or treatment planning may be declared a failure (requiring, e.g., larger manual adjustments to the treatment plan, which may be reviewed by the automatic planner to ensure that the adjusted plan does not violate safety constraints). Once treatment planning for the selected region is complete, the planner may present the treatment plan to the physician (step 126). The presentation may include an image (or series of image slices) of the region and surrounding areas, overlaid with graphics or supplemented with text indicating, e.g., the accumulated thermal dosage or temperature distribution, the transducer position, the order in which focal points are traversed, and/or whether efficacy and safety thresholds are satisfied. The physician may modify the plan (step 128), e.g., by changing the treatment order, re-defining treatment constraints, adjusting the treatment energy, or, if necessary, indicating a subregion for which treatment planning is to be repeated. When the physician finds the treatment plan acceptable, he may proceed to select another region for the next planning cycle (step 102), or commence actual treatment of the instant region, i.e., execute the plan (step 130).

Treatment of a region may be monitored (step 132), e.g., using MRI thermometry or direct temperature sampling with suitably positioned sensors. The measured temperature distribution may be compared with the predicted temperature distribution computed by the planner, and any discrepancies may be used to update the treatment plan. Since discrepancies typically arise from uncertainties or inaccuracies in the physical modeling underlying the simulation of the treatment and its effect, measurements taken during treatment are used, in some embodiments, to adjust one or more parameter values of the model(s). Adjustments may be made, first, to a parameter, or set of parameters, that has a particularly high uncertainty associated with it (and is therefore likely to need adjustment) and/or a change to which is known to affect the computed treatment effect greatly (i.e., a parameter to which the treatment effect is very sensitive, e.g., because the treatment effect is a higher-order rather than linear function of the parameter). For example, for ultrasound procedures, the acoustic absorption coefficient, or parameters defining its spatial distribution across the target, are typically good candidates for parameter adjustments. If re-computation of the treatment effect based on adjustments to the initially selected parameter(s) does not decrease the discrepancy satisfactorily, additional parameters may be changed. In some embodiments, the model parameters are ranked according to their uncertainties and/or the model sensitivity to the parameters to facilitate selection of one or more parameters for adjustment.

The selected model parameter(s) may be adjusted automatically based on the feedback, e.g., by fitting the model to the measurements. In some embodiments, fitting is based on measured iso-surfaces corresponding to respective constant temperatures or thermal doses. Further, to the extent that parameters vary as functions of other, space- and/or time-dependent quantities (e.g., the tissue type, which generally varies in space, or the temperature, which may change in time), the feedback may inherently encode information about such dependencies, e.g., in the form of spatial or temporal distributions of measured quantities. Parameter adjustment may also be based, at least partially, on human input, e.g., as provided by the physician monitoring treatment. Such human intervention may be assisted by intuitive visual representations of both predictions and measurements (e.g., in the form of boundaries indicating temperature or thermal-dose iso-surfaces and highlighting efficacy or safety thresholds). The displayed prediction may change dynamically in response to any user manipulation of parameter values. Parameter adjustments may be bounded by pre-set limits to prevent estimated values that are not physically realistic.

In some circumstances, the adjusted parameters can be propagated through the model to derive an updated treatment plan on the fly, whereas, in other situations, treatment may need to be interrupted to allow time to re-plan treatment of the region. The smaller the discrepancies between measurements and predictions are, the more feasible is typically an adjustment on the fly. An example of a straightforward adjustment to the treatment plan (i.e., an adjustment not requiring complete re-planning) is the increase, across all ultrasound stimuli, of the applied power to compensate, e.g., for a smaller absorption coefficient than previously assumed. If the current treatment results in incomplete coverage, but does not violate any clinical constraints, treatment need not be re-planned, but may be completed according to the previously created plan, and the same region may be revisited during the next (or some later) planning cycle to fill in gaps in coverage. Further, if the deviations between the predicted and the measured treatment effect are within a tolerable range, treatment of the currently treated region may continue, while subsequent planning stages for other regions may benefit from the feedback. Whether to continue or interrupt treatment may be decided by the treating physician. The physician may also take feedback into account when selecting the next region to be treated. In various embodiments, the physician deliberately selects regions for planning and treats them one at a time, using treatment results from the previously treated regions as feedback for treatment planning for the next region (e.g., by manually adjusting values of parameters used by the physical model).

While described above at the example of temperature measurements, the feedback provided during execution of the treatment plan is not limited to thermal feedback, but may also include acoustic or mechanical feedback, visual feedback (e.g., provided through MRI or another imaging technique), and/or feedback derived from measurements through analysis and calculations (e.g., of the accumulated thermal dose). Further, feedback received during treatment may include anatomical information and, importantly, information about any changes relative to the patient's anatomy as it existed at the time treatment was planned. Often, significant changes result from unavoidable patient motion during the treatment. Motion-tracking algorithms may be employed to detect deformations and positional changes of relevant target or non-target regions, and facilitate adjustments to the treatment plan (e.g., via image-registration algorithms) to compensate for such changes. Further, as movements and other changes are generally expected to occur during treatment (within certain limits), they may be taken into account by strategically planning the treatment, e.g., by specifying the order in which various regions are treated in a way that expected changes do not substantially increase treatment risk.

Monitoring the treatment may also involve documenting treatment progress, i.e., generating a treatment history in time. The treatment history may include anatomical images and, optionally, indications of special regions (e.g., heat-sensitive regions subject to constraints) therein, details of the applied treatment (such as values of planning parameters and/or indications of human interventions), as well as maps of the treatment effect (e.g., thermal maps indicating temperature or accumulated thermal dose). The treatment history is continuously adjusted to address any changes along treatment. Such changes may include, for example, tissue deformations and re-locations due to patient motion. The treatment history may be annotated with confidence levels indicating the accuracy of the gathered information, and may inform subsequent treatment. For example, it may be used to locate one or more regions that have not received sufficient treatment. A particular method of tracking tissue movements and updating the treatment history based on voxel-by-voxel tissue heat-tolerance attributes is described in U.S. patent application Ser. No. 13/194,286, entitled "Motion Compensation for Non-Invasive Treatment Therapies," filed on Jul. 29, 2011, which is hereby incorporated herein by reference in its entirety.

Figure 3:
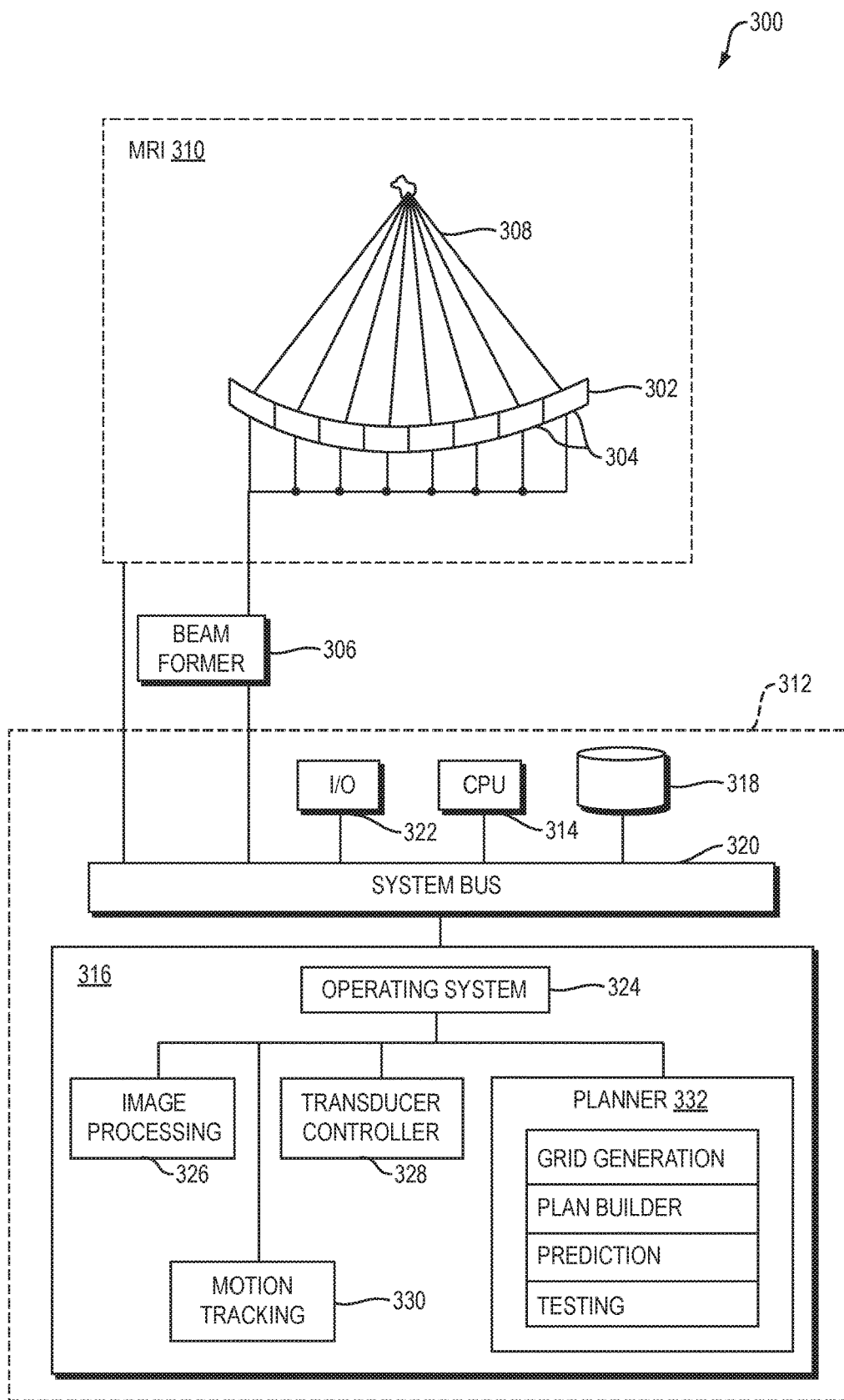
FIG. 3 is a block diagram illustrating a system for treatment planning in accordance with various embodiments.

FIG. 3 schematically illustrates an exemplary system 300 for planning and executing focused ultrasound treatment as described above. The system 300 includes an ultrasound transducer 302 comprising a one- or two-dimensional arrangement of transducer elements 304, which may, e.g., be piezoelectric ceramic elements. The transducer 302 may be curved (as shown) or planar, and may form a single surface, or include multiple discontiguous and, optionally, independently movable segments. The transducer elements 304 may be individually controllable, i.e., each element may be capable of emitting ultrasound waves at amplitudes and/or phases that are independent of the amplitudes and/or phases of the other transducer elements 304. Alternatively, the elements 304 may be grouped, and each group may be controlled separately. Collectively, the transducer elements 304 form a "phased array" capable of steering the ultrasound beam in a desired direction, and moving it during a treatment session based on electronic control signals provided by a beam former 306. The beam former 306 typically includes electronic control circuitry including amplifier and phase delay circuits for the transducer elements 304. It may split a radio-frequency (RF) input signal, typically in the range from 0.1 MHz to 4 MHz, to provide a plurality of channels for driving the individual transducer elements 304 (or groups thereof) at the same frequency, but at different amplitudes so that they collectively produce a focused ultrasound beam 308. The system 300 may also include other treatment apparatus; for instance, an active heater or cooling device (not shown) with a controllable temperature setting may complement ultrasound treatment by allowing a tissue surface to be held at a desired temperature. The system 300 may further include an MRI apparatus 310 (or other imaging device) that allows imaging a region of interest in the patient both prior to treatment for the purpose of treatment planning and during treatment for the purpose of guiding the ultrasound beam and monitoring treatment progress.

Further, the system 300 includes a computational facility, in communication with the beam former and the MRI apparatus, that facilitates treatment planning and adjustment. The computational facility may be implemented in any suitable combination of hardware, software, firmware, or hardwiring; in the illustrated embodiment, it is provided by a suitably programmed general-purpose computer 312. The computer may include a central processing unit (CPU) 314 and system memory 316, as well as, typically, one or more non-volatile mass storage devices 318 (such as one or more hard disks and/or optical storage units). The computer 312 further includes a bidirectional system bus 320 over which the CPU 314, memory 316, and storage devices 318 communicate with each other and with internal or external input/output devices, such as traditional user interface components 322 (including, e.g., a screen, a keyboard, and a mouse) as well as the beam former 306 and the MRI apparatus 310.

The system memory 316 contains instructions, conceptually illustrated as a group of modules, that control the operation of CPU 314 and its interaction with the other hardware components. An operating system 324 directs the execution of low-level, basic system functions such as memory allocation, file management and operation of mass storage devices 318. At a higher level, one or more service applications provide the computational functionality required for treatment planning and execution. For example, as illustrated, the system may include an image-processing module 326 for displaying, analyzing, and annotating images received from the MRI apparatus 310, a transducer control module 328 for computing the relative phases and amplitudes of the transducer elements 304, and a motion tracking module 330 for detecting and compensating for positional changes and deformations of tissues during the treatment.

Further, the system includes a treatment planner 332 that determines the sequence, locations, and treatment profile parameters of a series of sonications based on the processed images and user input; the resulting treatment plan may be used by the transducer controller 328 to determine the phase and amplitude settings. The treatment planner 332 may, itself, include a number of separate, but intercommunicating modules, such as a grid generator for computing a distribution of focal points over an identified region of the target (or, more generally, a focus-path generator), a plan builder for determining the order in which the focal points are traversed and treatment profile parameters associated with each point, a prediction module for simulating the treatment (e.g., based on physical and/or experimental models), and a testing module for computationally measuring parameters indicative of treatment coverage and compliance with imposed constraints (such as temperatures) at selected control points. As will be readily understood by a person of skill in the art, the computational functionality required to carry out treatment-planning methods in accordance herewith may be organized (in software modules or otherwise) in many different ways, and the depicted embodiment in FIG. 3 is, therefore, not to be regarded as limiting.

In general, the terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of performing focused-ultrasound treatment of a target tissue within a tissue region using a treatment system comprising a plurality of transducer elements each emitting a beam, the beams converging at a focal point or along a focus path, the method comprising:
    (a) creating a treatment plan at least in part by specifying (i) a focus pattern comprising a plurality of focal points or a plurality of focus paths where the beams of the treatment system will converge, each focal point or focus path corresponding to a different subregion of the target tissue to be treated, (ii) temporally variable ultrasound stimuli to be applied sequentially to create the plurality of focal points or the plurality of focus paths along the focus pattern, each ultrasound stimulus being associated with a focal point or a focus path, and (iii) at least one treatment constraint;
    (b) simulating treatment in accordance with a portion of the plan at least in part by computationally applying a first one of the temporally variable ultrasound stimuli to create a first one of the focal points or a first one of the focus paths corresponding to a first subregion of the target tissue;
    (c) computationally predicting an effect of the simulated treatment based, at least in part, on a physical model computationally modeling propagation of the effect;
    (d) comparing the predicted effect against the at least one treatment constraint;
    (e) when the at least one treatment constraint is violated, prior to simulating treatment in accordance with a remaining portion of the plan at least in part by computationally applying a second one of the temporally variable ultrasound stimuli to create a subsequent one of the focal points or a subsequent one of the focus paths specified in the treatment plan and corresponding to a second subregion of the target tissue different from the first subregion, altering the treatment plan, without altering the at least one treatment constraint, by adjusting at least one of the temporally variable ultrasound stimuli associated with a preceding focal point or a preceding focus path created prior to step (b) and corresponding to a third subregion of the target tissue different from the first and second subregions;
    (f) repeating steps (b) through (e) for the altered treatment plan; and
    (g) operating the treatment system to conduct the focused-ultrasound treatment in accordance with the altered treatment plan.

2. The method of claim 1, further comprising:
    (h) using the treatment system to conduct a first portion of the treatment in accordance with a first portion of the treatment plan;
    (i) experimentally monitoring the effect of the conducted treatment;
    (j) comparing the experimentally monitored treatment effect with the predicted treatment effect; and
    (k) upon detection of a discrepancy between the experimentally monitored treatment effect and the predicted treatment effect, adjusting the physical model and revising the treatment plan based on the adjusted model; and
    (l) conducting a second portion of the treatment in accordance with the revised treatment plan.

3. The method of claim 2, wherein adjusting the model comprises adjusting at least one parameter thereof.

4. The method of claim 3, wherein revising the treatment plan comprises repeating steps (a) through (g) with the adjusted model.

5. The method of claim 3, wherein the treatment plan is revised based on the adjusted model without repeating steps (a) through (g).

6. The method of claim 1, wherein creating the treatment plan further comprises defining parameters of a complementary treatment procedure.

7. The method of claim 6, wherein the complementary treatment procedure comprises active heating or cooling.

8. The method of claim 1, wherein steps (a) through (g) are successively carried out for a plurality of subregions of the target tissue.

9. The method of claim 1, wherein predicting the effect of the simulated treatment comprises modeling propagation of the effect into a different subregion of the target tissue or a non-target tissue within the tissue region.

10. The method of claim 1, wherein altering the treatment plan comprises altering at least one of the focus pattern or at least one of the ultrasound stimuli applied thereto.

11. The method of claim 1, wherein, following a comparison of the predicted effect against the at least one treatment constraint, the simulation is repeated for only a portion of the focus pattern and adjustments to the temporally variable ultrasound stimuli are confined to stimuli to be applied along that portion.

12. The method of claim 1, wherein the ultrasound stimuli vary between the focal points.

13. The method of claim 1, wherein the ultrasound stimuli vary along at least one of the focal paths.

14. The method of claim 1, wherein the at least one treatment constraint comprises at least one efficacy constraint and at least one safety constraint.

15. The method of claim 1, wherein the at least one treatment constraint comprises at least one of a tissue damage threshold, a treatment efficacy threshold, or geometric parameters of heat-sensitive tissues.

16. The method of claim 1, wherein the effect comprises heating of the tissue region due to ultrasound absorption and heat transport.

17. The method of claim 1, wherein the model comprises parameters of the tissue region.

18. The method of claim 17, wherein the model comprises at least one equation modeling ultrasound absorption and heat transport in the tissue region.

19. The method of claim 1, further comprising simulating treatment by computationally applying a third one of the temporally variable ultrasound stimuli so as to create said one of the focal points or one of the focus paths, the third one of the temporally variable ultrasound stimuli being applied in at least one preceding iteration.

20. The method of claim 19, further comprising altering the treatment plan by adjusting the third one of the temporally variable ultrasound stimuli associated with all preceding focal points or focus paths created prior to step (b).

21. The method of claim 1, wherein the at least one of the temporally variable ultrasound stimuli adjusted in step (e) is the same as the first one of the temporally variable ultrasound stimuli.

22. The method of claim 1, wherein the at least one of the temporally variable ultrasound stimuli adjusted in step (e) is different from the first one of the temporally variable ultrasound stimuli.

23. The method of claim 1, wherein in step (b), the effect of the simulated treatment is predicted by computationally modeling propagation of the effect into (i) non-target tissue within the tissue region and/or (ii) a subregion of the target tissue different from the first subregion.

24. A system for performing focused-ultrasound treatment of a target tissue within a tissue region, the system comprising:
a treatment system comprising a plurality of transducer elements each emitting a beam, the beams converging at a focal point or along a focus path;
a processor; and
memory storing (i) data descriptive of a model of the tissue region and at least one treatment constraint, (ii) a treatment plan specifying a focus pattern comprising a plurality of focal points or a plurality of focus paths where the beams of the treatment system will converge, each focal point or focus path corresponding to a different subregion of the target tissue to be treated and temporally variable ultrasound stimuli to be applied sequentially to create the plurality of focal points or the plurality of focus paths along the focus pattern, each ultrasound stimulus being associated with a focal point or a focus path, and (iii) instructions which, when executed by the processor, cause the processor to:
(a) simulate treatment in accordance with a portion of the stored treatment plan at least in part by computationally applying a first one of the temporally variable ultrasound stimuli to create a first one of the focal points or a first one of the focus paths corresponding to a first subregion of the target tissue;
(b) computationally predict an effect of the simulated treatment based on the data descriptive of the model of the tissue region and a physical model modeling propagation of the effect;
(c) compare the predicted effect against the at least one stored treatment constraint;
(d) when the at least one treatment constraint is violated, prior to simulating treatment in accordance with a remaining portion of the plan at least in part by computationally applying a second one of the temporally variable ultrasound stimuli to create a subsequent one of the focal points or a subsequent one of the focus paths specified in the stored treatment plan and corresponding to a second subregion of the target tissue different from the first subregion, alter the treatment plan, without altering the at least one treatment constraint, by adjusting at least one of the temporally variable ultrasound stimuli associated with a preceding focal point or a preceding focus path created prior to step (b) and corresponding to a third subregion of the target tissue different from the first and second subregions;
(e) repeat steps (a) through (d) for the altered treatment plan; and
(f) operating the treatment system to conduct the focused-ultrasound treatment in accordance with the altered treatment plan.

25. The system of claim 24, wherein in step (b), computationally predicting the effect of the simulated treatment comprises computationally modeling propagation of the effect into (i) non-target tissue within the tissue region and/or (ii) a subregion of the target tissue different from the first subregion.

26. A method of performing focused-ultrasound treatment of a target tissue within a tissue region using a treatment system comprising a plurality of transducer elements each emitting a beam, the beams converging at a focus location, the method comprising:
(a) electronically storing a treatment plan specifying (i) a treatment location pattern comprising a plurality of focus locations, each corresponding to a different subregion of the target tissue to be treated, (ii) temporally variable treatment stimuli to be applied sequentially to create the plurality of focus locations along the pattern, and (iii) at least one treatment constraint;
(b) using a computer, simulating treatment in accordance with a portion of the plan at least in part by computationally applying a first one of the temporally variable treatment stimuli to create a first focal point or a first focus path at a first one of the focus locations corresponding to a first subregion of the target tissue;
(c) computationally predicting an effect of the simulated treatment based on a physical model computationally modeling propagation of the effect;

(d) comparing the predicted effect against the at least one treatment constraint;

(e) when the at least one treatment constraint is violated, prior to simulating treatment in accordance with a remaining portion of the plan at least in party by computationally applying a second one of the temporally variable ultrasound stimuli to create a subsequent focal point or a subsequent focus path at a second one of the focus locations specified in the treatment plan a corresponding to a second subregion of the target tissue different from the first subregion, altering the treatment plan, without altering the at least one treatment constraint, by adjusting at least one of the temporally variable ultrasound stimuli associated with a preceding focus location associated with a second focal point or a second focus path created prior to step (b) and corresponding to a third subregion of the target tissue different from the first and second subregions;

(f) repeating steps (b) through (e) for the adjusted treatment plan; and (g) operating the treatment system to conduct the focused-ultrasound treatment in accordance with the adjusted treatment plan.

27. The method of claim 26, wherein the effect of the simulated treatment is predicted at least in part by computationally modeling propagation of the effect into (i) non-target tissue within the tissue region and/or (ii) a third focus location different from the first focus location in step (b).

* * * * *